Figure 5:
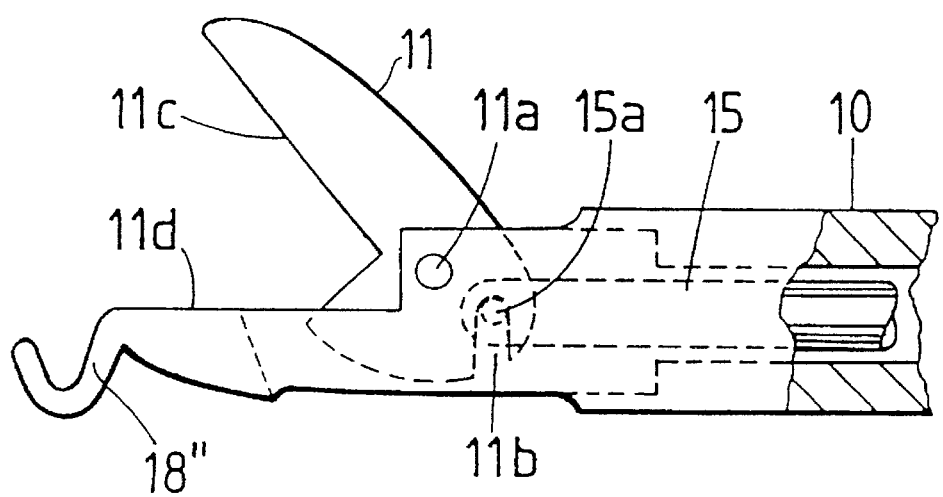

United States Patent [19]
Murphy

[11] Patent Number: 5,601,578
[45] Date of Patent: Feb. 11, 1997

[54] ENDOSCOPIC SUTURING DEVICE

[75] Inventor: Donald L. Murphy, Geelong, Australia

[73] Assignee: Miranic Investments Pty. Ltd., Geelong, Australia

[21] Appl. No.: 387,946
[22] PCT Filed: Aug. 26, 1993
[86] PCT No.: PCT/AU93/00434
  § 371 Date: Apr. 7, 1995
  § 102(e) Date: Apr. 7, 1995
[87] PCT Pub. No.: WO94/05217
  PCT Pub. Date: Mar. 17, 1994

[30] Foreign Application Priority Data

Aug. 28, 1992 [AU] Australia ................... PL4378
Mar. 2, 1993 [AU] Australia ................... PL7562

[51] Int. Cl.⁶ .................................... A61B 17/00
[52] U.S. Cl. .................... 606/148; 606/139; 606/207
[58] Field of Search ........................ 606/139, 144,
  606/145, 147, 148, 151, 205–208; 112/169,
  80.03; 81/300, 318, 418, 426, 424.5, 426.5;
  433/159

[56] References Cited

U.S. PATENT DOCUMENTS

| 86,016 | 1/1869 | Howell | 606/205 |
|---|---|---|---|
| 825,121 | 7/1906 | Frentzen | 606/139 |
| 2,678,650 | 5/1954 | Martone . | |
| 4,373,530 | 2/1983 | Kilejian . | |
| 4,641,652 | 2/1987 | Hutterer et al. . | |
| 4,683,885 | 8/1987 | Hutterer et al. . | |
| 4,836,205 | 6/1989 | Barrett . | |
| 5,147,373 | 9/1992 | Ferzli . | |
| 5,171,257 | 12/1992 | Ferzli . | |
| 5,181,919 | 1/1993 | Bergman et al. . | |
| 5,201,759 | 4/1993 | Ferzli . | |
| 5,211,650 | 5/1993 | Noda | 606/139 |
| 5,242,458 | 9/1993 | Bendel et al. | 606/147 |
| 5,257,637 | 11/1993 | El Gazayerli | 606/139 |
| 5,261,917 | 11/1993 | Hasson et al. | 606/148 |
| 5,383,877 | 1/1995 | Clarke | 606/139 |

FOREIGN PATENT DOCUMENTS

| 0537493 | 4/1993 | European Pat. Off. . | |
|---|---|---|---|
| 453256 | 1/1929 | Germany | 606/148 |
| 4218191 | 3/1993 | Germany . | |
| 923530 | 5/1982 | U.S.S.R. | 606/224 |
| 1034728 | 8/1983 | U.S.S.R. | 606/224 |
| 2157180 | 10/1985 | United Kingdom . | |

Primary Examiner—Jeffrey A. Schmidt
Attorney, Agent, or Firm— Larson and Taylor

[57] ABSTRACT

An endoscopic suturing device comprising an elongate hollow tube, one end of which carries a thread engaging and loop forming member and a thread or needle jaw member. An actuating member at the other end of the tube engages an elongate actuating rod extending through the tube and is coupled to the thread or needle jaw member, whereby axial movement of the actuating member against the biasing action of a spring causes the actuating rod to actuate the thread or needle clamping member. The device is capable of disassembly for easy cleaning and sterilization.

9 Claims, 3 Drawing Sheets

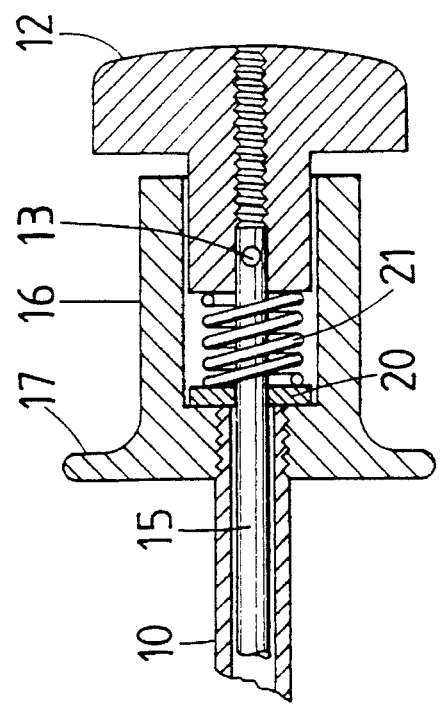
FIG 1
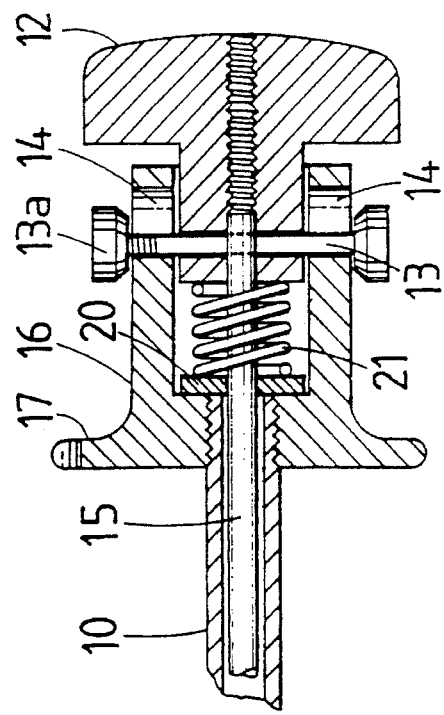
FIG 2
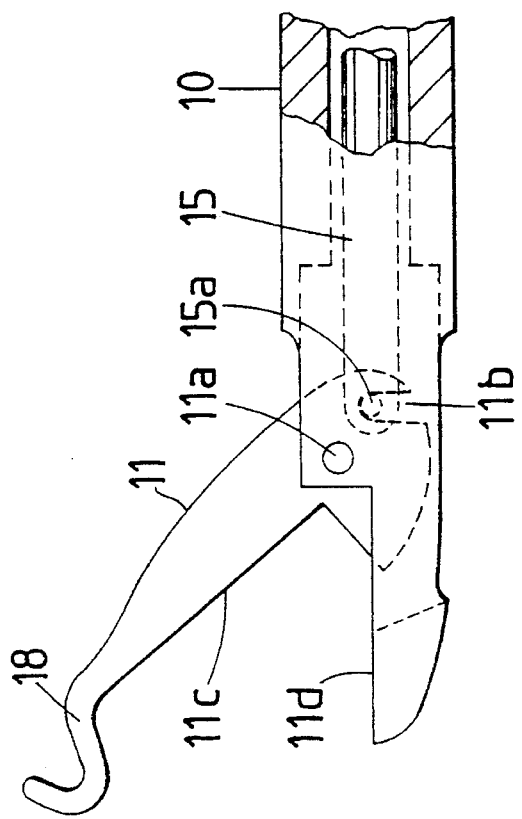
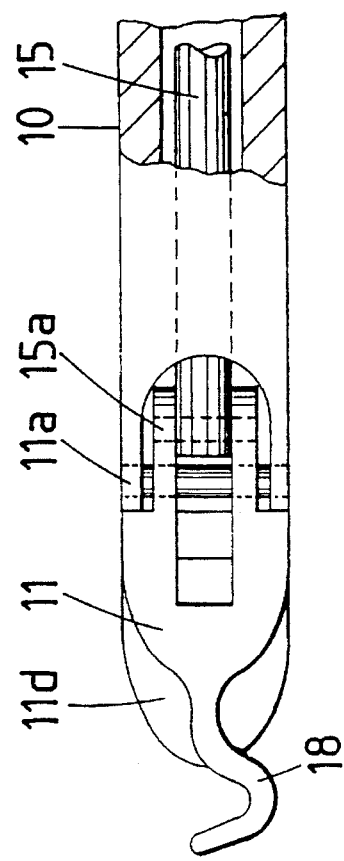

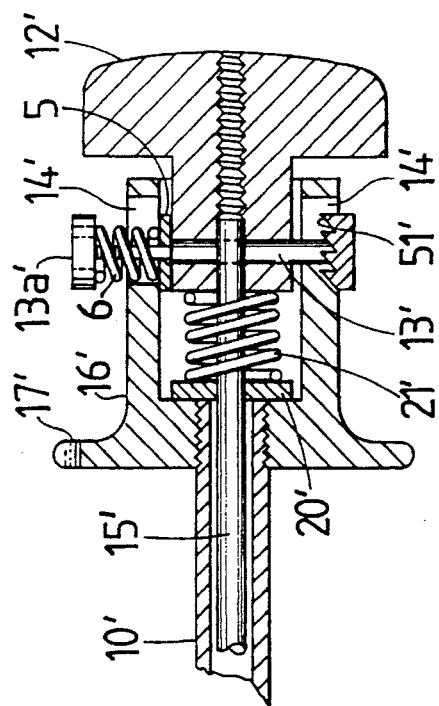
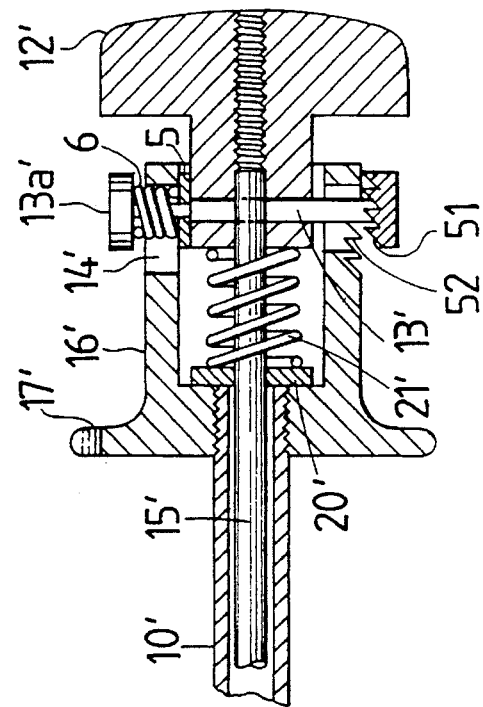
FIG 3
FIG 4
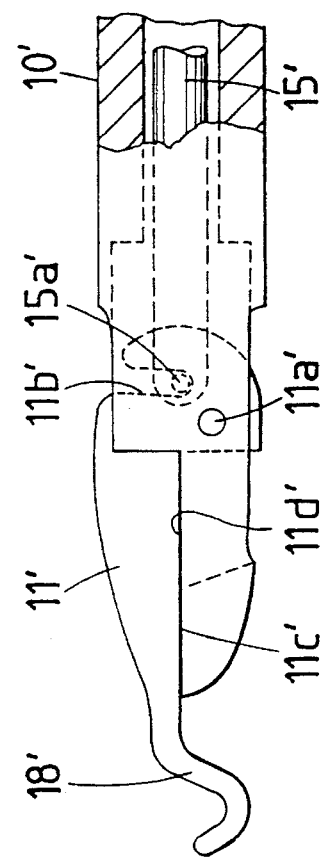
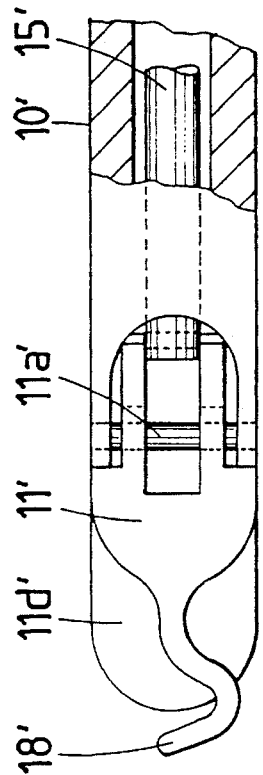

ENDOSCOPIC SUTURING DEVICE

This invention relates to endoscopic suturing and in particular a device or instrument for forming knots to tie tissue together in cavities within animal (human) bodies to complete internal surgical procedures.

It has become practice with certain surgical procedures within cavities in the human body to avoid over intrusive surgical techniques, involving large incisions to gain access to body cavities, to now use a surgical technique known as endoscopy where relatively small incisions are made through to the body cavity and surgical procedures are carried out using an endoscope being an elongate device or instrument in the nature of a telescope inserted thorough the incision to view the area where surgery is being carried out, whilst a similar elongate device or instrument is used to sever internal body tissue during various types of tissue removal or repair operations. By using such a less intrusive surgical technique involving small incisions, patient tram is kept to a minimum resulting in a lesser tern of hospitalisation and keeping scarring to a minimum.

However one of the major difficulties with such a surgical technique arises when it is necessary to suture internal body tissue by stitching the tissue together using thread like material, which requires the formation of knots within the body cavity as distinct from externally accessible areas where suturing external body tissue is involved.

One presently used technique involves the use of clips or clamps which clamp the body tissue together and which are applied within the body cavity using an elongate clip applicator inserted through one of the external incisions whilst the viewing the application of the clip with the endoscope through another external incision. However, some such clips are not designed to be dissolved over a period of time whilst the joined body tissue heals and as a result are relatively expensive adding significantly to the cost of the surgical procedure.

One other known intracorporal suturing technique involves the use of a pair of instruments one being in the form a pair suture grasping forceps and a separate knotting device, and involves inserting the suture (thread) through the tissue to be joined using a needle holder and thereafter holding one free end of the thread with the needle holder whilst through a separate incision the knotting device is inserted to catch the thread between the needle holder and the tissue whereby by rotating the knotting device through one or more rotations of 180°, one or more loops are formed in the thread, whereafter either through the same incision by withdrawing the knotting device, or thorough a separate incision, the suture grasping forceps are inserted to grasp the other end of the thread and draw it through the loop or loops to form a single or multiple knot.

It is therefore an object of present invention to provide an endoscopic suturing device which will suture together body tissue in an internal body cavity and which is not subject to the same problems and difficulties as the aforementioned suturing techniques.

In accordance with the present invention there is provided an endoscopic suturing device, comprising an elongate hollow tube one end of which carries a combination of a thread engaging and loop forming member and a thread or needle clamping member, and means operable at the other end of the tube for actuating the thread or needle clamping member, wherein said means for actuating the thread clamping member comprises an actuating member engaging an elongate actuating rod extending through said tube and coupled to said thread or needle clamping member, whereby axial movement of the actuating member causes said actuating rod to actuate said thread or needle clamping member.

Such a device enables the instrument to complete a knotting function in one operation and whilst inserted through the same incision, to grasp the short end of the thread by the thread clamping member on the needle side of the tissue to be joined, whereafter rotation of the device through one or more rotations in a predetermined direction around the long end of the thread on the needle side of the tissue to be joined, being a mirror image of the manner in which a knot would otherwise be instrument tied, to form one or more loops about the device. Through another access incision, any grasping instrument or a second endoscopic suturing device's thread engaging and loop forming member can be manipulated to engage the short end of the thread on the other side of the tissue to be joined and draw the thread through the one or more loops to form half a knot. Whereafter rotation of the device through one or more rotations in a predetermined direction around the long end of the thread again to form one or more loops about the device. Any grasping instrument or the initial thread engaging and loop forming member can then be manipulated to engage the short end of the thread and draw the thread through the one or more loops to complete the knot.

Two preferred embodiments of the invention will now be described with reference to the accompanying drawings, in which:

FIG. 1 is a side elevational view partially sectioned of a first embodiment of the suturing device, FIG. 2 is a plan view partially sectioned of the device of FIG. 1, FIG. 3 is a side elevation plan view partially sectioned of a second embodiment of the suturing device in one operational mode thereof, FIG. 4 is a plan view partially sectioned of the second embodiment of FIG. 3 in another operational mode thereof; and FIG. 5 is a side elevation view of a portion of a third embodiment of the suturing device.

The respective drawings illustrate only the extreme ends of the devices and with the ends carrying the thread engaging and loop forming and thread or needle clamping arrangement enlarged for the sake of clarity.

The endoscopic suturing device of the embodiment of FIGS. 1 and 2 of the drawings comprises an elongate hollow tube 10 within one end of which a clamping member in the form a jaw member 11 is mounted to pivot about a pivot pin 11a between a closed position, and an open position as shown in FIGS. 1 and 2. The jaw member 11 is adapted to be opened and closed by an elongate actuating rod 15, such as in a bowden cable arrangement, which rod 15 carries a pin 15a which detachably engages within a slot 11b in the end of the clamping member on one side of the pivot pin 11a with the clamping member having a clamping surface 11c which engages during closing of the clamping member with a cooperating clamping surface 11d on the end of the hollow tube 10. The other end of the elongate actuating rod 15 is connected to an actuating member 12 via a connecting bolt 13 the opposite ends of which bolt pass through elongate slots 14 in the wall of a cylindrical housing 16 and which allow axial movement of the actuating member 12. The housing 16 has a finger grasping flange 17 extending around the circumference thereof and upon axial movement of the actuating member, and as a result of axial movement of the elongate actuating rod 15 within the tube 10, the jaw member 11 is caused to open.

In order to bias the actuating member 12, and as a consequence jaw member 11 via the elongate rod 15, to the closed position, a compression coil spring 21 is provided surrounding the end of the elongate rod 15 within the housing 16 and between a stop and gas seal 20, freely slidable along the elongate actuating rod 15, and the actuating member 12, whereby upon release of pressure on the actuating member the coil spring 21 will act to bias the clamping member 11 back to a position whereby a thread or needle will be clamped between the clamping surfaces 11c and 11d.

In this embodiment, the extreme end of the clamping member 11 carries a thread engaging and loop forming member in the form a spiral hook 18. As shown in FIG. 5, the relative disposition of the hook 18 and jaw member 11 may be interchanged, and the spiral may be in any direction. In the embodiment of FIG. 5, in which like numerals indicate like elements of the embodiment of FIG. 1, spiral hook 18" is carried at the outer end of clamping surface 11d no the end of hollow tube 10.

In addition, the use of the biasing spring member 21 may be eliminated whereby the surgeon may manipulate opening and closing of the clamping member 11 without the assistance of a biasing spring, and such an alternative mechanism may involve the utilisation of an internal or external ratchet mechanism or friction slide.

The connecting bolt 13 carries a nut 13a which when loosened and removed allows the bolt 13 to be removed, whereafter the actuating member 12, coil spring 21, gas seal washer 20 and actuating rod 15 can be axially withdrawn from within the hollow tube 10 after disengaging the pin 15a from the slot 11b in the end of the clamping member. The components of the device are thus separated from each other for cleaning and sterilisation purposes.

In the second embodiment of FIGS. 3 and 4 of the drawings, the device once again comprises an elongate hollow tube 10' within one end of which a clamping member in the form of a jaw member 11' is mounted to pivot about a pivot pin 11a' between a closed position as shown in FIG. 3 and an open position as shown in FIG. 4. The jaw member 11' is adapted to be opened and closed by an elongate actuating rod 15', such as a bowden cable arrangement, which rod 15' carries a pin 15a' which detachably engages within a slot 11b' in the end of the clamping member on one side of the pivot pin 11a' with the clamping member having a clamping surface 11c' which engages during closing of the clamping member with a cooperating clamping surface 11d' on the end of the hollow tube 10'. The other end of the elongate actuating rod 15' is connected to an actuating member 12' via a connecting bolt 13' the opposite ends of which bolt pass through elongate slots 14' in the wall of a cylindrical housing 16' and which allow axial movement of the actuating member 12'. The housing 16' has a finger grasping flange 17' extending around the circumference thereof and upon axial movement of the actuating member, and as a result axial movement of the elongate actuating rod 15' within the tube 10' the jaw member 11' in this embodiment is caused to close as the pin 15a' and slot 11b' arrangement is on the side of the pivot pin 11a' opposite to that of the embodiment of FIGS. 1 and 2.

In order to bias the actuating member 12' and as a consequence the jaw member 11' via the elongate rod 15' to the open position, a compression coil spring 21' is provided surrounding the end of the elongate rod 15' within the housing 16' and between a stop and gas seal 20', freely slidable along the elongate actuating rod 15', and the actuating member 12', whereby upon release of pressure on the actuating member the coil spring 21' will bias the clamping member 11' back to a non-clamping position.

The extreme end of the clamping member 11' carries a thread engaging and loop forming member in the form of a spiral hook 18', although the relative disposition of the hook 18' and the jaw member 11' may be interchanged in other embodiments, and the spiral maybe in any direction.

The connecting bolt 13' carries a nut 13a' which when loosened and removed allows the bolt 13' to be radially removed, whereafter the actuating member 12', coil spring 21', gas seal washer 20' and actuating rod 15' can be axially withdrawn from within the hollow tube 10' after disengaging the pin 15a' from the slot 11b' in the end of the clamping member. The components of the device are thus once again separated from each other for cleaning and sterilisation purposes.

In the second embodiment of the invention, the head of the bolt 13' has formed on its underside a saw tooth configuration 51 which matingly engages with a similar saw tooth configuration 52 on the external surfaces of the housing 16' adjacent one of the slots 14', whereby when the actuating member 12' is forced inwardly of the housing the saw tooth configuration 51 will ride over the mating configuration 52 until the clamping position of the clamping member 11' is achieved at which time engagement of the configurations 51 and 52 will occur with the assistance of a compression coil spring 6 surrounding the bolt 13' and sandwiched between the nut 13a' on the other end of the bolt and extending through the adjacent slot 14' to a stop 5 freely slidable along the bolt 13' and engaging the side of the actuating member or alternatively engaging the bottom of a recess containing and surrounding the slot 14'. In order to release the clamping member from the clamping position shown in FIG. 3 so as to move to the open position shown in FIG. 4, the nut 13a' is depressed to axially shift the bolt and disengage the two saw tooth configurations 51 and 52, whereafter the compression coil spring 21' acts to move the actuating member and elongate rod to a position whereby the clamping member returns to its open position.

The suturing devices of the two embodiments of the invention are operable to perform a surgical suturing procedure as described previously.

Although not shown in the drawings, the elongate tube 10 or 10' may be tapered toward the operating end or stepped at a point along its length to provide a reduced diametre part of its length toward the operating end.

I claim:

1. An endoscopic suturing device, comprising an elongate hollow tube, one end of which includes, as part thereof, a thread engaging and loop forming spiral hook member and a thread or needle jaw member, and means operable at the other end of the tube for actuating said jaw member, said means for actuating said jaw member comprising an actuating member engaging an elongate actuating rod extending through said tube and coupled to said jaw member, whereby axial movement of the actuating member causes said actuating rod to actuate said jaw member.

2. An endoscopic suturing device as claimed in claim 1, further comprising a fixed clamping member at said one end of said tube, and wherein said thread or needle jaw member is supported adjacent said fixed clamping member.

3. An endoscopic suturing device as claimed in claim 2, wherein said thread engaging and loop forming member is integral with said jaw member.

4. An endoscopic suturing device as claimed in claim 2, wherein said thread engaging and loop forming member is integral with said fixed clamping member.

5. An endoscopic suturing device as claimed in claim 1, wherein axial movement of said actuating member and said actuating rod causes said thread or needle jaw member to move to a non-clamping position.

6. An endoscopic suturing device as claimed in claim 5, wherein a biasing means is provided between the actuating member and the adjacent end of the elongate tube to bias the thread or needle jaw member to a clamping position.

7. An endoscopic suturing device as claimed in claim 1, wherein axial movement of said actuating member and said actuating rod causes said thread or needle jaw member to move to a clamping position.

8. An endoscopic suturing device as claimed in claim 7, wherein means are provided to hold said thread or needle jaw member in said clamping position.

9. An endoscopic suturing device as claimed in claim 1, wherein the connections between the actuating rod and the jaw member, as well as between the actuating rod and the actuating member, are detachable so that the device can be disassembled to allow cleaning and sterilization of its various components.

* * * * *